(12) United States Patent
Meyerson et al.

(10) Patent No.: US 10,827,931 B2
(45) Date of Patent: Nov. 10, 2020

(54) PATCH FOR TEMPERATURE DETERMINATION

(71) Applicant: Welch Allyn, Inc., Skaneateles Falls, NY (US)

(72) Inventors: Craig M. Meyerson, Syracuse, NY (US); David E. Quinn, Auburn, NY (US); Zhon Ye Chu, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 257 days.

(21) Appl. No.: 15/395,533

(22) Filed: Dec. 30, 2016

(65) Prior Publication Data

US 2018/0184908 A1 Jul. 5, 2018

(51) Int. Cl.
| | | |
|---|---|---|
| *A61B 5/01* | (2006.01) | |
| *A61B 5/00* | (2006.01) | |
| *G01K 13/00* | (2006.01) | |
| *G01K 7/42* | (2006.01) | |

(52) U.S. Cl.
CPC .............. *A61B 5/015* (2013.01); *A61B 5/489* (2013.01); *A61B 5/6833* (2013.01); *G01K 7/427* (2013.01); *G01K 13/002* (2013.01); *A61B 2560/0412* (2013.01); *A61B 2562/0276* (2013.01); *A61B 2562/046* (2013.01); *A61B 2562/12* (2013.01); *A61B 2562/18* (2013.01)

(58) Field of Classification Search
CPC ....... A61B 5/015; A61B 5/6833; A61B 5/489; A61B 2562/12; A61B 2562/046; A61B 2560/0412; A61B 2562/0276; A61B 2562/18; G01K 7/427; G01K 13/002
See application file for complete search history.

(56) References Cited

U.S. PATENT DOCUMENTS

| | | | |
|---|---|---|---|
| 5,816,706 A * | 10/1998 | Heikkila | G01K 1/16 374/134 |
| 2008/0167573 A1 | 7/2008 | Stivoric et al. | |
| 2009/0306536 A1 | 12/2009 | Ranganathan et al. | |
| 2011/0158284 A1* | 6/2011 | Goto | A61B 5/0008 374/163 |
| 2011/0317737 A1* | 12/2011 | Klewer | G01K 1/16 374/29 |
| 2012/0024833 A1* | 2/2012 | Klewer | A61B 5/0008 219/211 |
| 2012/0109571 A1* | 5/2012 | Shimizu | G01K 1/165 702/130 |

(Continued)

FOREIGN PATENT DOCUMENTS

WO   WO2012170177   12/2012

OTHER PUBLICATIONS

PCT Search Report and Written Opinion dated Apr. 20, 2018 for PCT Application No. PCT/US17/69159, 22 pages.

(Continued)

*Primary Examiner* — Rene T Towa
(74) *Attorney, Agent, or Firm* — Lee & Hayes, P.C.

(57) ABSTRACT

A wearable patch includes a first portion comprising a first material, a second portion comprising a second material different from the first material, a first temperature sensor disposed proximate a first surface of the patch, and a second temperature sensor disposed proximate an additional surface of the patch.

23 Claims, 8 Drawing Sheets

(56) References Cited

U.S. PATENT DOCUMENTS

2012/0143079 A1* 6/2012 Lia .......................... A61B 5/01
                                                    600/549
2014/0207405 A1    7/2014 Heller
2014/0221796 A1    8/2014 Lia et al.

OTHER PUBLICATIONS

The Extended European Search Report dated Jul. 2, 2020 for European Patent Application No. 17886443.5, 7 pages.

* cited by examiner

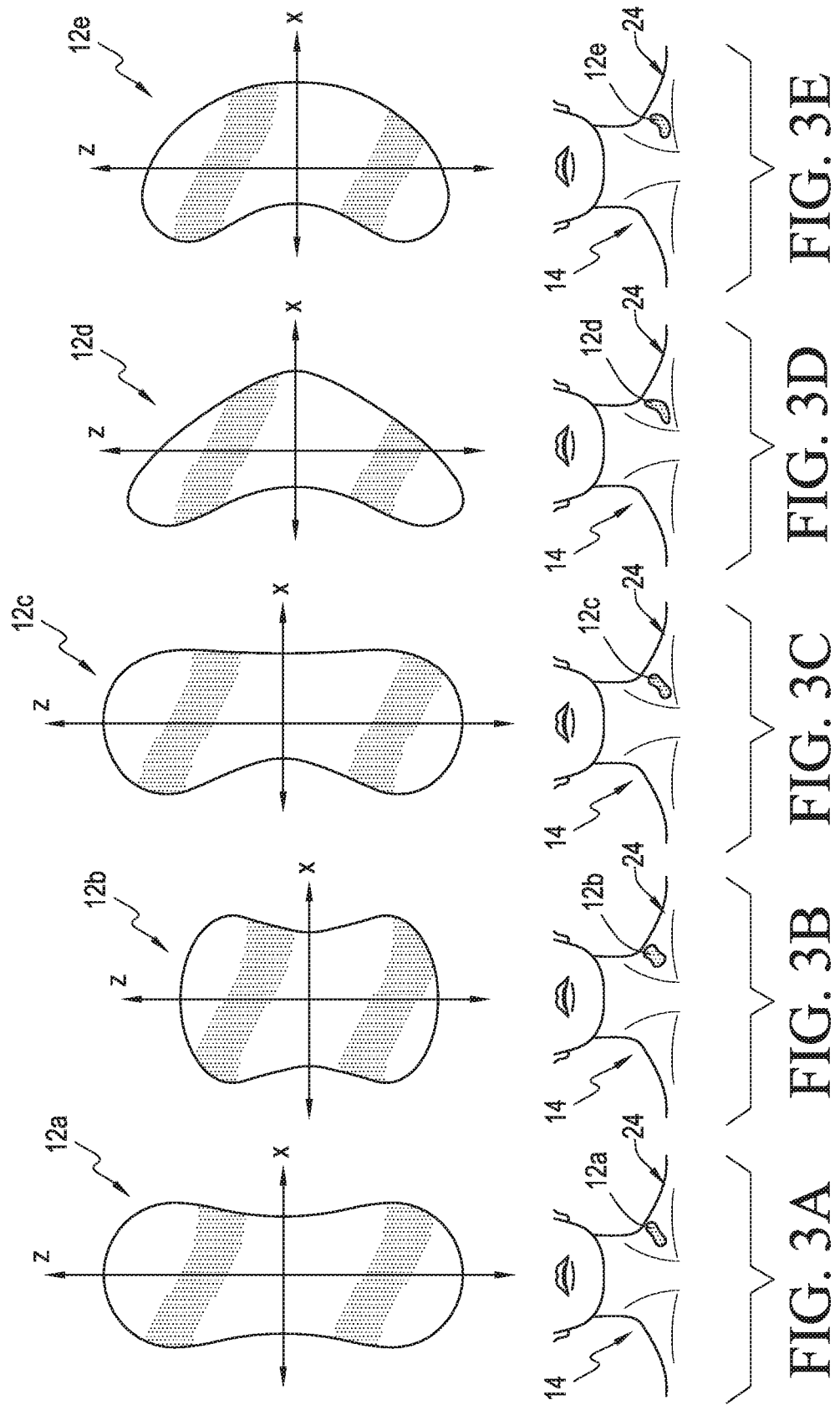

PATCH FOR TEMPERATURE DETERMINATION

CROSS-REFERENCE TO RELATED APPLICATIONS

Not applicable.

STATEMENT REGARDING FEDERALLY SPONSORED RESEARCH OR DEVELOPMENT

None.

REFERENCE TO A "SEQUENCE LISTING"

Not applicable.

BACKGROUND OF THE INVENTION

Field of the Invention

The present disclosure generally relates to devices and methods for temperature determination and, in particular, to wearable patches configured for use in determining a temperature.

Description of Related Art

Body temperature is widely used by physicians and other healthcare professionals as an indicator of a person's health. In most healthcare facilities, various non-invasive techniques may be utilized to measure temperature before, during, and/or after treatment. Such techniques typically include the use of oral, rectal, tympanic, or axial thermometers. These instruments are useful in providing a substantially instantaneous temperature reading, but are not generally used to provide continuous, relatively long-term monitoring of a patient's temperature. However, it is this continuous temperature measurement, or the determination of relatively sudden changes in patient temperature that is most useful to healthcare professionals when providing treatment. Such devices are not well-suited for continuous temperature measurement since, for example, disposing a thermometer in the mouth of a patient for long periods of time can cause discomfort and can be otherwise cumbersome. Moreover, often the condition of the patient may make it difficult or impossible to access, for example, the mouth, rectum, and/or other areas of the body where temperature is typically measured with such devices.

To overcome some of these problems, devices have been developed enabling continuous monitoring of patient temperature. Such devices are typically in the form of an adhesive patch or bandage-like structure having one or more temperature sensors. Such devices are typically adhered to the patient's skin overlaying a portion of an artery or other blood vessel. These devices, however, are characterized by deficiencies making them undesirable for use in many patient treatment settings. For example, such devices must be placed in close proximity to a blood vessel in order to obtain an accurate temperature measurement. However, since such blood vessels are located beneath the skin, and are not easily visible, such devices are often mispositioned on the patient. Such mispositioning can have adverse affects on the accuracy of the temperature measurement obtained using such devices. In addition, the temperature at the skin surface can be significantly influenced by the ambient temperature and often does not correlate well with core body temperature. Moreover, variations in the thermal resistance of the skin caused by, among other things, the opening and closing of arterioles, may also reduce the accuracy of the body temperature estimation if not properly accounted for.

The example embodiments of the present disclosure overcome one or more of the deficiencies described above. Additionally, the example embodiments of the present disclosure relate to example processes, systems, and/or devices disclosed in co-owned U.S. Pat. No. 8,657,758, the entire disclosure of which is expressly incorporated herein by reference.

BRIEF SUMMARY OF THE INVENTION

In an example embodiment of the present disclosure, a wearable patch includes a first portion comprising a first insulative material, the first portion including a first surface and a second surface opposite the first surface. The patch also includes a second portion comprising a second material different from the first material, the second portion including a third surface extending substantially coplanar with the first surface. The patch further includes a first temperature sensor embedded substantially within the first material of the first portion and disposed adjacent to the first surface, and a second temperature sensor embedded substantially within the second material of the second portion and disposed adjacent to the third surface. In such embodiments, when the patch is disposed on a skin surface of a patient such that the first surface is disposed closer to the skin surface than the second surface, a difference between a first temperature of the skin surface determined by the first temperature sensor and a second temperature of the skin surface determined by the second temperature sensor is indicative of an orientation of the patch relative to a blood vessel disposed proximate the skin surface.

In an additional embodiment of the present disclosure, a method includes determining a first temperature, of a skin surface of a patient, with a first temperature sensor of a wearable patch, wherein the first temperature is determined when the patch is disposed on the skin surface, and the skin surface comprises a skin surface of the patient. In such a method, the patch includes a first portion comprising a first insulative material, the first portion including a first surface and a second surface opposite the first surface, the first temperature sensor being embedded substantially within the first portion adjacent to the first surface, and a second portion comprising a second material different from the first material, the second portion including a third surface extending substantially coplanar with the first surface, the first material having a first thermal resistance, and the second material having a second thermal resistance less than the first thermal resistance. Such an example method also includes determining a second temperature of the skin surface with a second temperature sensor of the patch, wherein the second temperature is determined when the patch is disposed on the skin surface, and the second temperature sensor is embedded substantially within the second portion adjacent to the third surface. The method further includes determining a difference between the first and second temperatures, wherein the difference is indicative of an orientation of the patch relative to a blood vessel disposed proximate the skin surface, determining a correction factor based on the difference, and determining a core temperature of the patient based on the first temperature, the second temperature, and the correction factor.

In a further example embodiment of the present disclosure, a method of manufacturing a system Includes providing a first insulative material having a first thermal resistance, the first material including a first surface and a second surface opposite the first surface. The method also includes providing a second material different from the first material and having a second thermal resistance less than the first thermal resistance, and joining the first material and the second material to form a wearable patch such that a third surface of the second material extends substantially coplanar with the first surface. The method further includes embedding a first temperature sensor substantially within the first material such that the first temperature sensor is disposed adjacent to the first surface. The method also includes embedding a second temperature sensor substantially within the second material such that the second temperature sensor is disposed adjacent to the third surface and the second temperature sensor is substantially thermally isolated from the first portion. In such embodiments, when the first and third surfaces are disposed on a skin surface of a patient, a difference between a first temperature of the skin surface determined by the first temperature sensor and a second temperature of the skin surface determined by the second temperature sensor is indicative of a position of at least one of the first and second sensors relative to a blood vessel disposed proximate the skin surface.

BRIEF DESCRIPTION OF THE SEVERAL VIEWS OF THE DRAWING(S)

FIG. 3A illustrates a top view of an example patch, and a corresponding illustration of the example patch disposed on a skin surface of a patient, according to an embodiment of the present disclosure.

FIG. 3B illustrates a top view of an example patch, and a corresponding illustration of the example patch disposed on a skin surface of a patient, according to another embodiment of the present disclosure.

FIG. 3C illustrates a top view of an example patch, and a corresponding illustration of the example patch disposed on a skin surface of a patient, according to still another embodiment of the present disclosure.

FIG. 3D illustrates a top view of an example patch, and a corresponding illustration of the example patch disposed on a skin surface of a patient, according to yet another embodiment of the present disclosure.

FIG. 3E illustrates a top view of an example patch, and a corresponding illustration of the example patch disposed on a skin surface of a patient, according to a further embodiment of the present disclosure.

DETAILED DESCRIPTION OF THE INVENTION

Figure 1:
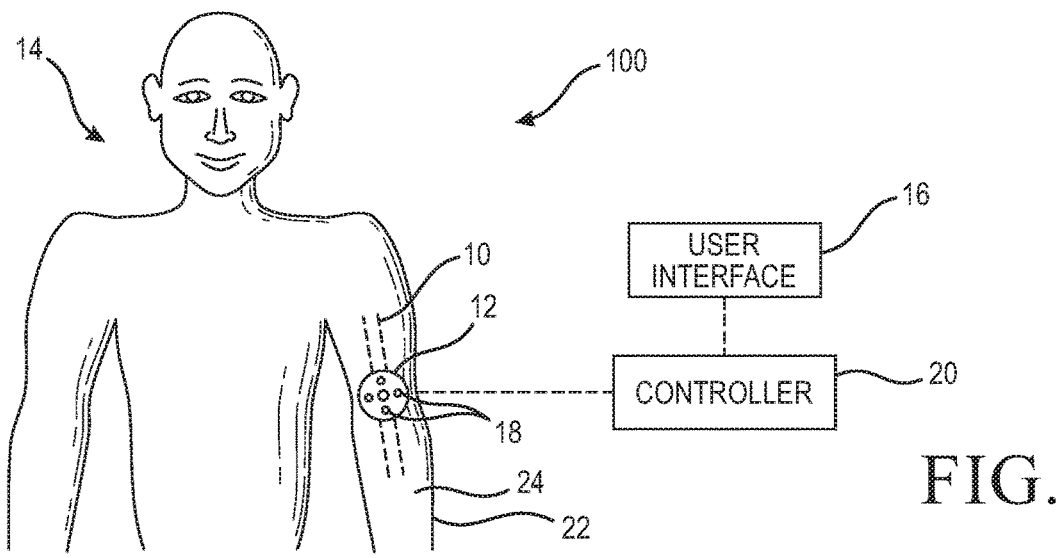
FIG. 1 illustrates a system according to an example embodiment of the present disclosure.

FIG. 1 illustrates an example system 100 of the present disclosure. The system 100 may, for example, comprise a patient monitoring system, a temperature determination system, or any other like system configured to monitor a patient and, in some embodiments, to determine a temperature and/or a hemodynamic parameter of the patient. As used herein, the term "hemodynamic parameter" can include any indication of cardiac or vascular health, such as, for example, an indication of cardiac, circulatory, or vascular functionality. In some examples, a hemodynamic parameter may include a heart rate, a blood pressure, a blood vessel compliance, an aortic index, an augmentation index, a reflected wave ratio, or an indication of treatment. Additionally, the temperatures sensed, measured, calculated, estimated, and/or otherwise determined by the system may comprise skin surface temperatures, internal or "core" temperatures, and/or any other temperature of a patient. For purposes of the present disclosure, embodiments in which the system 100 is configured to determine one or more temperatures of a patient and/or a core temperature of the patient will be described below unless otherwise noted.

As shown in FIG. 1, the system 100 may include one or more example temperature measurement devices configured to be disposed proximate a vessel 10 of a patient such as an artery, vein, capillary, or other type of blood vessel. For example, the system 100 may include one or more patches 12 useful in determining the temperature of a subject 14. Such subjects 14 may be, for example, human beings in need of medical treatment or diagnosis, and in some examples, the subject 14 may be a patient of a healthcare professional. Accordingly, in some examples described herein, the subject 14 may be referred to as a "patient." The system 100 may also include a user interface 16 operably connected to the patch 12, a plurality of sensors 18 operably connected to the patch 12, and/or a controller 20 operably connected to at least one of the patch 12 and the user interface 16.

As shown in FIG. 1, the patch 12 may be removably connected, attached, affixed, disposed on, adhered, and/or otherwise connected to a limb 22 of the subject 14. For example, the patch 12 may be temporarily connected to and/or may temporarily contact at least a portion of an arm, a leg, or other limb 22 during use. In particular, the patch 12 may be disposed on and/or removably attached to a skin surface 24 of the limb 22. Alternatively, the patch 12 may be temporarily connected to and/or may temporarily contact the forehead, the clavicle, and/or any other body part or corresponding skin surface 24 of the subject 14 during use. Accordingly, the patch 12 may be removably attached to any skin surface 24 of the subject, and removably attaching the patch 12 to any of the skin surfaces 24 described herein may assist in the determination of a core temperature and/or any other like internal body temperature of the subject 14. Thus, while several of the Figures described herein illustrate the patch 12 being removably attached to a limb 22 of the subject 14, it is understood that such Figures are not intended to limit the present disclosure to attaching the patch 12 to the skin surface 24 of such limbs 22.

The user interface 16 may include one or more buttons, switches, keypads, dials, knobs, and/or other like devices configured to assist in controlling one or more functions of the patch 12 and/or the controller 20. Such user interfaces 16 may be useful in, for example, energizing and/or deenergizing one or more components of the patch 12, toggling through and/or selecting one or more modes of operation or display, enabling and/or disabling one or more alarms or signals associated with patch operation, initiating a single instantaneous core temperature determination, initiating a substantially continuous and/or repeating core temperature determinations, and/or other like modes, functions, or operations.

Additionally, the user interface 16 may include a liquid crystal diode (LCD) screen, a light emitting diode (LED) display, a digital read-out, and/or any other like display device. Such a display device of the user interface 16 may be configured to, for example, indicate and/or otherwise output the determined temperature of the subject 14 during operation of the patch 12. The user interface 16 may be configured to display the temperature substantially instantaneously and/or substantially continuously depending on the mode of operation of the patch 12 and/or of the controller 20. The display device of the user interface 16 may be, for example, a substantially numerical digital display, and may also be configured to display any other typical operating information such as, for example a temperature vs. time trend line or other graphical depiction.

The controller 20 may be configured to control the operation of each component of the patch 12 and/or of the use interface 16. In some embodiments, the controller 20 may comprise one or more processors, memory components, I/O devices, wired and/or wireless communication devices, and/or other computer, server, and/or electronic computing device components known in the art. In an example embodiment, the controller 20 may be configured to receive signals, information, measurements, and/or other data from the one or more sensors 18 of the patch 12, and to calculate and/or otherwise determine a core temperature of the subject 14 based on the information received. In any of the examples described herein, the controller 20 may include, may be connected to, and/or may be in communication with a hard drive, a memory stick, an SD card, a removable memory device, network and/or cloud-based memory, and/or any other computer-readable storage device (not shown). Such a computer-readable storage device may include instructions stored thereon that, when executed by a controller 20, cause the controller 20 to perform various operations, including any of the steps, processes, determinations, calculations, selections, and/or other operations described herein.

The controller 20 may also be configured to execute one or more commands and/or control programs. Such commands and/or control programs may include and/or may comprise the instructions described above, and may be stored on the computer-readable storage device. For example, the controller 20 may be programmed to initiate one or more alarms in response to determining a core temperature that is greater than or equal to a predetermined threshold temperature. In addition, the controller 20 may be configured to initiate such an alarm during a substantially continuous core temperature calculation operation if the calculated core temperature increases and/or decreases at a rate that is greater than or equal to a predetermined threshold temperature change rate. In such an embodiment, the controller 20 may substantially continuously calculate a core temperature change rate, and the threshold temperature and/or the threshold temperature change rate may be indicative of the onset of infection and/or of a decline in the health of the subject 14. In an example embodiment, such a threshold temperature may be approximately 100° F. and such a threshold change rate may be approximately 0.02° F./minute. In additional examples, the threshold temperature and/or the threshold change rate may be greater than or less than the example temperature and change rate noted above. The controller 20 may also initiate such an alarm to indicate that a location and/or orientation of the patch 12 should be changed, and such a location and/or orientation change alarm may be initiated in response to one or more sensed metrics indicative of blood flow beneath the skin surface 24. Such metrics may include, for example, various skin surface temperatures measured by the respective sensors 18 of the patch 12.

The patch 12 may also include one or more additional components not illustrated in FIG. 1. For example, in some embodiments the patch 12 may include one or more lights, LEDs, speakers, sirens, and/or other like devices configured to emit an audible and/or optical alarm or signal in response to a command or signal from the controller 20. As described above, such an alarm or other signal may be initiated by, for example, the controller 20 when the calculated temperature meets or exceeds a threshold temperature. In additional example embodiments, such an alarm or signal may be initiated during a substantially continuous temperature calculation operation where the rate of core temperature change meets or exceeds the predetermined core temperature change rate threshold.

Additionally, the patch 12 may include one or more transponders, transceivers, or other components configured to receive signals, power, or information from a remote source, such as a remote controller 20 or the like. Such components of the patch 12 may also include one or more devices configured to transmit signals, data, and/or other information to remote receivers. For example, an example transponder may be configured to transmit information corresponding to one or more sensed temperatures to a remote computer, controller 20, or other like device utilized in the calculation of core temperatures of the subject 14. Such an example transponder may facilitate communication with remote devices using, for example, radio, infrared, wireless, WI-FI®, BLUETOOTH®, ZIGBEE® near field communication, and/or other technologies. Accordingly, such a transponder may enable monitoring of subjects 14 fitted with the patch 12 from one or more remote locations within, for example, a hospital or other healthcare facility. In addition, such a transponder may facilitate a wireless internet connection with one or more routers, servers, or the like. Further, although not shown in FIG. 1, it is understood that example patches 12 may also include one or more USB ports, communication terminals, or other like components configured to facilitate connecting the patch 12 to one or more computers, controllers 20, user interfaces 16, monitors, servers, routers, or other like monitoring devices via one or more cables, wires, leads, or other like connection devices.

Figure 2:
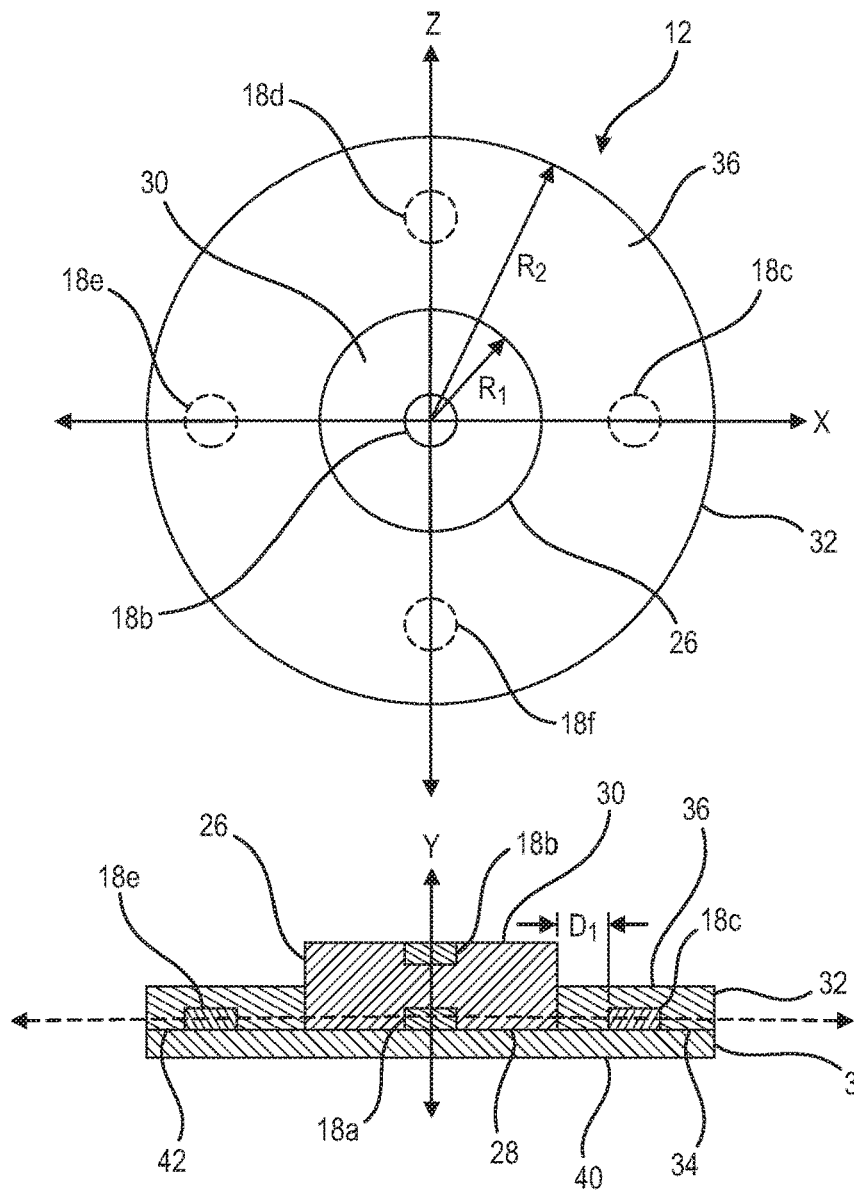
FIG. 2 illustrates a top view of a patch according to an example embodiment of the present disclosure.
Figure 3:
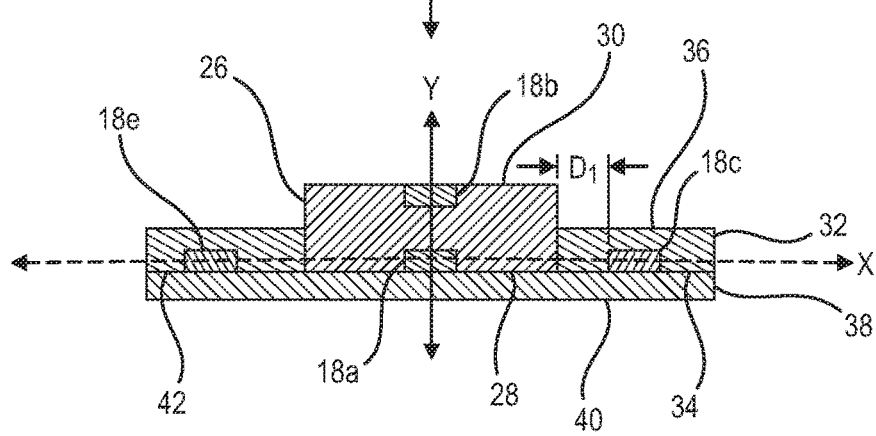
FIG. 3 illustrates a cross-sectional view of the patch shown in FIG. 2.

As shown in FIGS. 2 and 3, an example patch 12 may include a first portion 26, and the first portion 26 may include a first surface 28 and a second surface 30 opposite the first surface 28. The patch 12 may also include a second portion 32, and the second portion 32 may include a third surface 34 and a fourth surface 36 opposite the third surface 34. In example embodiments, the third surface 34 may extend substantially coplanar with the first surface 28. Additionally, at least one of the first surface 28 and the third surface 34 may extend substantially parallel to a longitudinal axis of the patch 12. Such a longitudinal axis may comprise the X axis shown in FIGS. 2 and 3, and/or the Z axis shown in FIG. 2. In such examples, at least one of the first surface 28 and the third surface 34 may extend substantially perpendicular to a transverse axis of the patch 12. Such a transverse axis may comprise the Y axis shown in FIG. 3. In any of the examples described herein, one or more of the sensors 18 may be disposed substantially along at least one of a longitudinal and/or a transverse axis of the patch 12.

In some examples, the patch 12 may also include a base layer 38 disposed adjacent to and/or connected to the first and third surfaces 28, 34. In particular, the base layer 38 may include a fifth surface 40 configured to at least temporarily contact and/or be removably connected to the skin surface 24 of the subject 14. The base layer 38 may also include a sixth surface 42 disposed adjacent to and/or connected to at least one of the first and third surfaces 28, 34. As will be described below, the base layer 38 may comprise a relatively thin layer, wall, film, and/or other like barrier or piece of material extending between the skin surface 24, and the first and third surfaces 28, 34 while the patch 12 is removably connected to the skin surface 24. The base layer 38 may assist in protecting one or more of the sensors 18 from contaminants, bodily fluids, infectious and/or contagious elements, wet conditions, and/or other potentially damaging or harmful environmental elements. In alternative embodiments, on the other hand, the base layer 38 may be omitted and the first and third surfaces 28, 34 may be configured to be removably connected to the skin surface 24. Further, the second and fourth surfaces 30, 36 may be configured to be exposed to ambient conditions such as, for example, ambient air or other like environments in a hospital and/or other healthcare facility.

The first and second portions 26, 32 of the patch 12 may be made from any substantially rigid medically approved material known in the art. Such materials may include, for example, plastics, rubber, polymers, synthetic materials, cloth, mesh, and/or combinations thereof. For example, the patch 12 and/or portions thereof may be made from materials similar to removable bandages or other like materials. These materials may allow for breathability during use and for easy disposal once use is complete. In addition, such patch materials may be substantially flexible, substantially light-weight, and/or relatively comfortable such that a patch 12 may be disposed on and/or removably attached to the skin surface 24 of a subject 14 for extended periods of time. In some examples, the first portion 26 may comprise a first insulative material and the second portion 32 may comprise a second material, such as a second insulative material, different from the first material. Such insulative materials may be, for example electrically and/or thermally insulative.

The first and second portions 26, 32 may be formed using any known manufacturing process. For example, at least one of the first and second portions 26, 32 may be formed through a molding, extrusion, pressing, or other process. Further, the first and second portions 26, 32 may be connected via any of the above processes or by adhesion, welding, heat sealing, or other known processes.

In some examples, the first portion 26 may be substantially cylindrical and may have a first radius R1, and in such examples the second portion 32 may be substantially annular and may have a second radius R2 greater than the first radius R1. In such embodiments, the first radius R1 may be substantially equal to an inner radius of the second portion 32 while the second radius R2 may be substantially equal to an outer radius of the second portion 32. While FIGS. 2 and 3 illustrate the first portion 26 as being substantially cylindrical, and the second portion 32 as being substantially annular and substantially surrounding a perimeter of the first portion 26, in further embodiments the first and second portions 26, 32 may be substantially cube-shaped, substantially rectangular, and/or any other convenient shape or configuration. Various additional example configurations of the patch 12 are illustrated in FIGS. 3a-3e. In particular, FIG. 3a illustrates an example patch 12a having an elongated configuration with a width along the X axis that is less than a corresponding width at locations spaced from the X axis. FIG. 3b illustrates an example patch 12b having a shape similar to the patch 12a, but with a relatively shorter length along the Z axis. FIG. 3c illustrates an example patch 12c having an elongated configuration with a substantially linear side that extends substantially parallel to the Z axis. FIG. 3d illustrates an example patch 12d having a boomerang shape. FIG. 3e illustrates an example patch 12e having a substantially bean-shaped configuration. Further, each of the FIGS. 3a-3e illustrate the respective patches 12a-12e being disposed on and/or removably attached to a skin surface 24 of the subject 14, and in FIGS. 3a-3e, the skin surface 24 is proximate the clavicle. The various shapes, sizes, orientations, and/or other configurations of the example patches 12a, 12b, 12c, 12d, 12e illustrated in FIGS. 3a-3e may improve patient comfort, ease of placement on a respective skin surface 24 and/or other measurement site, and durability of the patches 12a, 12b, 12c, 12d, 12e. Such configurations may result in improved signal fidelity, improved temperature measurement accuracy, and/or other performance improvements over the period of time in which the respective patches 12a, 12b, 12c, 12d, 12e are worn by the subject 14.

With continued reference to FIG. 3, to assist with removably attaching the patch 12 to the skin surface 24, any known adhesive may be disposed on at least a portion of the first surface 28 and/or at least a portion of the third surface 34. In further embodiments in which the patch 12 includes the base layer 38, any known adhesive may be disposed on at least a portion of the fifth surface 40 of the base layer 38. Alternatively, one or more elastic straps, bands, belts, ties, or the like may be connected to at least a portion of the patch 12 to assist in removably attaching the patch 12 to the skin surface 24.

The patch 12 may have a known thermal resistance, and such thermal resistance may depend upon, for example, the thickness of the patch 12 and/or the one or more materials utilized to form the patch 12. For example, the thermal resistance of the plastics, rubber, polymers, or other materials used to form the first and second portions 26, 32 of the patch 12 may be known in the art, and the core temperatures described herein may be determined based upon the known thermal resistances of the first and second portions 26, 32. Additionally, as illustrated in the cross-sectional view of FIG. 3, the first portion 26 may have a first thickness extending substantially perpendicularly from the first surface 28 to the second surface 30, and the second portion 32 may have a second thickness extending substantially perpendicularly from the third surface 34 to the fourth surface 36. In some examples, the first thickness may be different from the second thickness, and the thermal resistances of the first and second portions 26, 32 may be based at least in part on the first and second thicknesses, respectively. In example embodiments, the thermal resistance of the first portion 26 may be greater than the thermal resistance of the second portion 32.

As noted above, the patch 12 may include one or more sensors 18, and FIGS. 2 and 3 illustrate an example embodiment in which the patch 12 includes six sensors (labeled as 18a-18f). In other example embodiments, the patch 12 may include greater than or less than six sensors 18. For example, in some embodiments one or more of the sensors 18 illustrated in FIGS. 2 and 3 may be omitted, while in other embodiments one or more additional sensors 18 may be included in the patch 12.

In example embodiments, one or more of the sensors 18 may comprise a thermocouple, a thermistor, a thermometer, a resistance temperature detector (RTD), and/or any other like device useful in measuring temperature. In additional example embodiments, such a sensors 18 may comprise any temperature sensitive material or coating known in the art. In additional example embodiments, the sensors 18 may be configured to sense, measure, and/or otherwise detect one or more additional properties, conditions, and/or characteristics of the subject 14. For example, in addition to temperature, the sensor 18 may be configured to detect heart rate, blood pressure, electrical current, and the like.

The various sensors 18 of the patch 12 may be disposed at any location on or within the patch 12 convenient for assisting in determining one or more temperatures of the patch 12, of the skin surface 24 on which the patch 12 is disposed, and/or of an ambient environment in which the patch 12 is being used. For example, one or more of the sensors 18 may be embedded substantially within the patch 12, such as substantially within the first portion 26 or substantially within the second portion 32. In such embodiments, the one or more sensors 18 may be integral with the patch 12. Alternatively, the one or more sensors 18 may be substantially internal to the patch 12 such that the one or more sensors 18 may be positioned and/or otherwise configured to sense a temperature or other characteristic of at least part of the patch 12.

In any of the embodiments described herein, at least one of the sensors 18 may be substantially exposed to and/or disposed at least partly in contact with the skin surface 24 of the subject 14 while the first and third surfaces 28, 34 of the patch 12 are in contact with the skin surface 24. Alternatively, in example embodiments in which the patch 12 includes the base layer 38 described above, the base layer 38 may form at least a portion of the first and third surfaces 28, 34 and/or may overlay at least a portion of the first and third surfaces 28, 34. In such embodiments, the thermal resistance of the base layer 38 may be substantially negligible so as to maximize the accuracy of the one or more measurements made by the sensors 18. Alternatively, the thermal resistance of the base layer 38 may be known or empirically determined, and this thermal resistance may be taken into account when calculating the core temperature of the subject 14.

In example embodiments of the present disclosure, the patch 12 may include a first sensor 18a disposed within the first portion 26, and at least one additional sensor 18c, 18d, 18e, 18f spaced longitudinally or radially (e.g., along one of the X axis or the Z axis) from the first sensor 18a and disposed within the second portion 32. Spacing the sensors 18 in this way may assist in determining the extent to which the thermal resistance of the first portion 26 affects the temperatures determined by the first sensor 18a disposed within the first portion 26.

Additionally, spacing the sensors 18 longitudinally or radially from the first portion 26 may minimize the insulating effect of the first portion 26 on the sensors 18 disposed outside of the first portion 26. For example, as shown in FIGS. 2 and 3, at least one of the additional sensors 18c, 18d, 18e, 18f may be spaced longitudinally or radially from, for example, a perimeter of the first portion 26 by a distance D1. Such spacing may minimize and/or substantially eliminate the effect that the thermal resistance of the first portion 26 has on the temperatures determined by the at least one of the additional sensors 18c, 18d, 18e, 18f. For example, at least one of the additional sensors 18c, 18d, 18e, 18f may be spaced longitudinally or radially from the first portion 26 by a distance D1 such that the at least one of the additional sensors 18c, 18d, 18e, 18f is substantially thermally isolated from the first portion 26.

As shown in at least FIGS. 2 and 3, a first sensor 18a may be disposed at and/or otherwise adjacent to the first surface 28 of the first portion 26. Additionally, at least one of the additional sensors 18c, 18d, 18e, 18f may be disposed at and/or otherwise adjacent to the third surface 34 of the second portion 32. Further, in some embodiments, the patch 12 may include at least one additional sensor 18b disposed at and/or otherwise adjacent to the second surface 30 of the first portion 26. For example, the sensor 18b may be disposed along the Y axis of the patch 12 extending substantially perpendicular from the X and Z axes, and in such embodiments, a temperature determined by the sensor 18b may comprise and/or may be indicative of a temperature of an ambient environment in which the patch 12 is being used. Absolute temperatures determined by any of the sensors 18 described herein may be used to determine a core temperature of the subject 14 based at least in part on a thermal resistance of at least one of the first portion 26 and the second portion 32. Additionally, differences between or averages of temperatures determined by any of the sensors 18 described herein may also be used to determine a core temperature of the subject 14 based at least in part on such thermal resistances.

Figure 4:
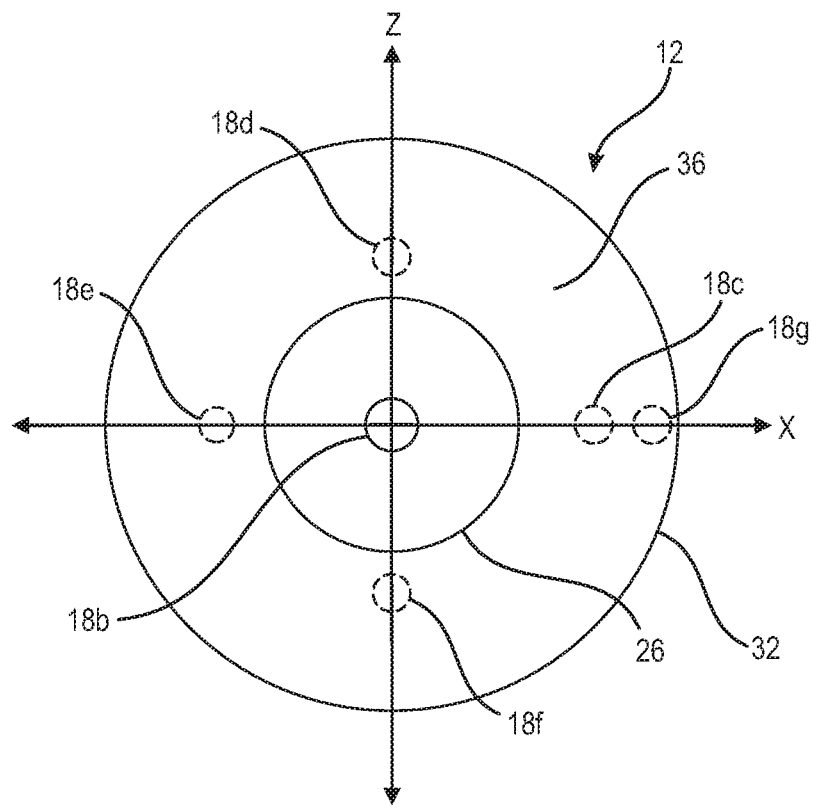
FIG. 4 illustrates a top view of a patch according to another example embodiment of the present disclosure.
Figure 5:
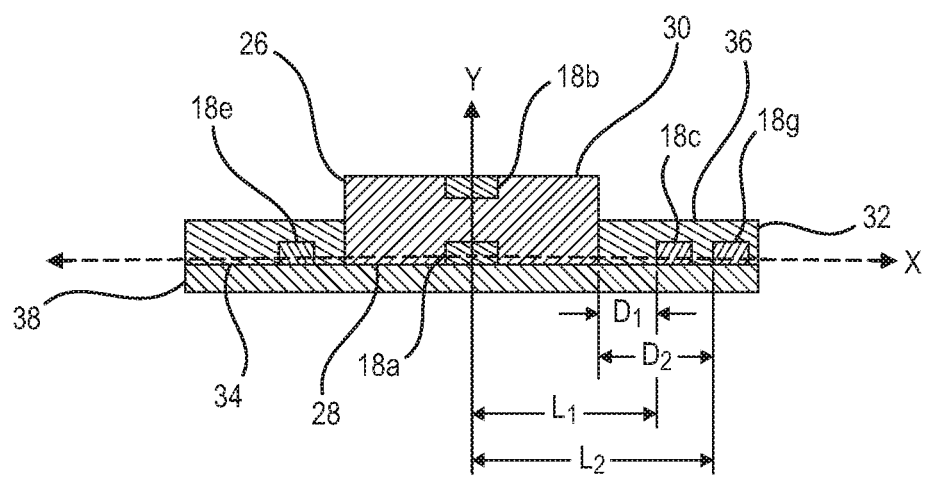
FIG. 5 illustrates a cross-sectional view of the patch shown in FIG. 4.

FIGS. 4 and 5 illustrate a further example embodiment of the present disclosure in which the patch 12 includes at least one additional sensor 18g disposed radially or longitudinally outward of the sensor 18c along the X axis. While FIGS. 4 and 5 illustrate a single additional sensor 18g, it is understood that such example embodiments may include any number of additional sensors 18. For example, at least one additional sensor 18g may be disposed radially or longitudinally outward of at least one of the sensors 18d, 18e, and 18f. In such embodiments, such an additional sensor 18g may assist in determining if, and the extent to which, an adjacent radially inward sensor 18c, 18d, 18e, 18f is affected by the thermal resistance and/or other insulating effects of the first portion 26. For example, it is understood that as blood flows beneath and/or within the skin surface 24, a skin surface temperature determined by the sensor 18a may be greater than a skin surface temperature determined by the sensor 18c due at least in part to the thermal resistance of the first portion 26 be greater than the thermal resistance of second portion 32. In such examples, a difference in a skin surface temperature determined by the sensor 18c and a corresponding skin surface temperature determined by the sensor 18g may be indicative of the accuracy and/or reliability of the skin surface temperature determined by the sensor 18c. Accordingly, such a difference may be utilized to determine the extent to which one or more temperatures determined by the sensor 18a and/or 18c should be modified or corrected, such as by a correction factor, when determining a corresponding core temperature of the subject 14.

As noted above, one or more of the sensors 18c, 18d, 18e, 18f may be spaced from the first portion 26 by any desirable distance D1 along, for example, the X axis or Z axis in order to substantially thermally isolate the one or more sensors 18c, 18d, 18e, 18f from the first portion 26. In a similar way, one or more of the additional sensors 18g described herein may also be spaced from the first portion 26 by any desirable distance D2 along, for example, the X axis or Z axis in order to substantially thermally isolate the one or more additional sensors 18g from the first portion 26. Further, as shown in FIG. 5 with respect to the sensor 18c, one or more of the sensors 18c, 18d, 18e, 18f may be spaced from the Y axis by any desirable distance L1 along, for example, the X axis or Z axis, and one or more of the additional sensors 18g described herein may also be spaced from the Y axis by any desirable distance L2 along, for example, the X axis or Z axis. In such example embodiments, any of the temperatures determined by the one or more sensors 18 may be utilized as inputs in determining the core temperature of the subject 14. Likewise, differences between, and/or averages of any such temperatures may also be utilized as inputs in the core temperature determination. In such examples, one or more of the distances D1, D2, L1, L2 may also be used as inputs in such core temperature determinations.

FIGS. 6-9 illustrate example schematic views of a patch 12 disposed at different locations and/or orientations on the skin surface 24 of a limb 22. Likewise, FIGS. 6a-9a illustrate corresponding example schematic cross-sectional views of the limb 22 and patch 12 shown in FIGS. 6-9, respectively. As will be described with respect to these Figures, in some examples the skin surface temperatures determined by one or more of the sensors 18 may be indicative of an orientation of the patch 12 relative to, for example, a blood vessel 10 disposed within the limb. 22 of the subject 14 on which the patch 12 is disposed. While FIGS. 6-9 and 6a-9a illustrate the patch 12 being disposed on a skin surface 24 of a limb 22, as noted above, in additional examples, the patch 12 may be removably attached to any skin surface 24 of the subject (e.g., to a skin surface 24 of the forehead, a skin surface proximate the clavicle, and/or of other measurement sites on the subject's body). In any of the examples described herein, the skin surface temperatures determined by the one or more sensors 18 may be indicative of an orientation of the patch 12 relative to a blood vessel 10 disposed beneath such a skin surface 24, such as a blood vessel 10 disposed proximate the skin surface 24. For ease of description, however, the example limb 22 illustrated in FIGS. 6-9 and 6a-9a will be described for the duration of this disclosure unless otherwise noted.

In any of the examples described herein, skin surface temperatures determined by one or more of the sensors 18 may also be indicative of a direction, and/or orientation of blood flow within the limb 22. For instance, temperature sensors 18 within the same portion 26, 32 of the patch 12 may determine respective skin surface temperatures, and a comparison of such skin surface temperatures may be indicative of the orientation of blood flow within the limb 22 and/or the orientation of patch 12 relative to the vessel 10. In some examples, the controller 20 and/or other components of the system 100 may be configured to determine the orientation of blood flow within the limb 22, the orientation of patch 12 relative to the vessel 10, and/or the orientation of one or more sensors 18 relative to the vessel 10 based at least in part on such comparisons. Further, the controller 20 and/or other components of the system 100 may be configured to use values, measurements, angles, metrics, and/or other information indicative of the orientation of blood flow within the limb 22, the orientation of patch 12 relative to the vessel 10, and/or the orientation of one or more sensors 18 relative to the vessel 10 as inputs in determining at least one of a correction factor, a thermal resistance of a skin layer of the limb 22, and the core temperature of the subject 14.

For example, as will be discussed in greater detail below, in examples in which one or more of sensors 18c, 18d, 18e, 18f disposed relatively closer to the outer circumference of the portion 32 determine higher temperatures relative to corresponding measurements made by one or both of the sensors 18a, 18b, the controller 20 may determine that one or more of sensors 18c, 18d, 18e, 18f is disposed closer to the vessel 10 (i.e., relatively closer to a flow of blood) than one or both of the sensors 18a, 18b. In such examples, the controller 20 may weigh measurements made by one or more of the sensors 18c, 18d, 18e, 18f more heavily in a temperature determination algorithm than corresponding temperature measurements made by one or both of the sensors 18a, 18b. Additionally, it is understood that the difference between temperature measurements made using the inner-most (e.g., most heavily insulated) sensor 18a and one or more of the sensors 18c, 18d, 18e, 18f disposed relatively closer to the outer circumference of the portion 32 can be indicative of the overall thermal flow (e.g., blood flow) under the patch 12. For example, a relatively high thermal flow beneath the patch 12 may result in a relatively small difference, while a relatively high thermal flow beneath the patch 12 may result in a relatively large difference.

As illustrated in at least FIGS. 6a-9a, radial distances D3, D4, D5 between the vessel 10 (e.g., an outer surface of the vessel 10) and respective sensors 18 of the patch 12 may vary based on the location and/or orientation of the patch 12 on the skin surface 24. Such radial distances D3, D4, D5 may also depend upon the location of the vessel 10 within the limb 22. In some examples, variations in the radial distances D3, D4, D5 may have a corresponding effect on skin surface temperatures determined by the respective sensors 18. Additionally, as will be described below, the alignment and/or orientation of the various sensors 18 relative to the vessel 10 may also have a corresponding effect on skin surface temperatures determined by the respective sensors 18 and, in some embodiments, may be indicative of the orientation of blood flow within the limb 24.

Figure 6:
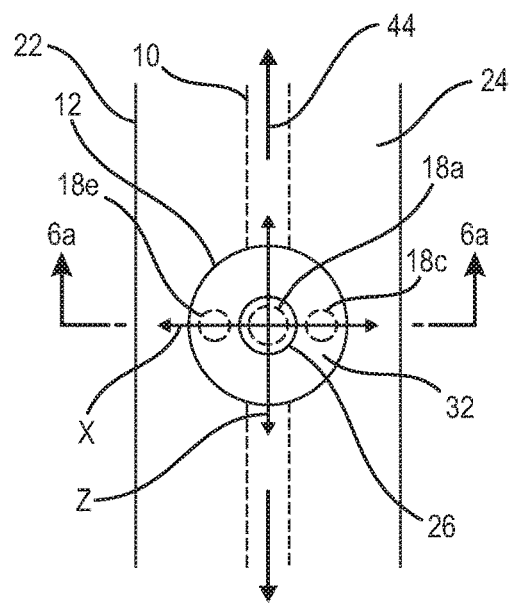
FIG. 6 illustrates an example patch disposed on a skin surface of a patient according to an example embodiment of the present disclosure.
Figure 6A:
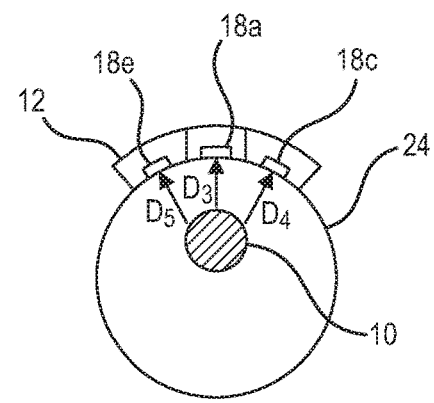
FIG. 6A illustrates a schematic cross-sectional view of the patch shown in FIG. 6.

FIG. 6 illustrates an example embodiment in which a patch 12 includes a sensor 18a embedded substantially within the first portion 26, and additional sensors 18c, 18e, embedded substantially within the second portion 32 and spaced from the sensor 18a longitudinally along the X axis. FIG. 6A illustrates a cross-section of the limb 24 and patch 12 shown in FIG. 6. In the embodiment of FIGS. 6 and 6A, the Z axis of the patch 12 is aligned with and/or extends substantially parallel to a longitudinal axis 44 of the vessel 10. Additionally, the X axis of the patch 12 extends substantially transverse to the longitudinal axis 44 of the vessel 10. In such examples, the distance D4 between the sensor 18c and the vessel 10 may be substantially equal to the distance D5 between the sensor 18e and the vessel 10. As a result, assuming that the thermal resistance of the body tissue between the vessel 10 and the patch 12 is relatively constant, skin surface temperatures measured by the sensors 18c, 18e may be substantially equal. Further, a difference between a skin surface temperature measured by one or both of the sensors 18c, 18e, and a corresponding skin surface temperature measured by sensor 18a may be indicative of the orientation of the patch 12 and/or the sensors 18a, 18c, 18e relative to the blood vessel 10.

For example, if the difference between a skin surface temperature measured by one or both of the sensors 18c, 18e and a corresponding skin surface temperature measured by the sensor 18a is greater than a predetermined threshold temperature, the controller 20 and/or other components of the system 100 may determine that the X axis of the patch 12, along which the sensors 18a, 18c, 18e are disposed, extends substantially transverse to the longitudinal axis 44 of the vessel 10. In such examples, the determined orientation of the patch 12 may also be based, at least in part, on the thermal resistance of a skin layer and/or body tissue of the limb 22. Further, in such examples, temperature measurements obtained using one or more of the sensors 18d, 18f, 18h described herein may also be used by the controller 20 and/or other components of the system 100 to determine the orientation of the patch 12 illustrated in FIGS. 6 and 6a.

Figure 7:
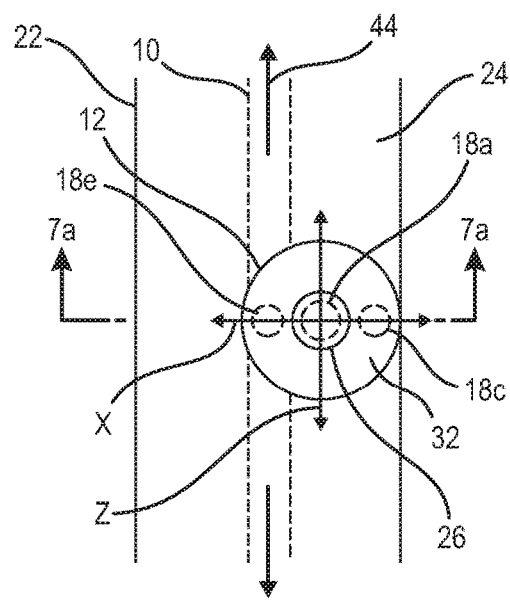
FIG. 7 illustrates an example patch disposed on a skin surface of a patient according to another example embodiment of the present disclosure.
Figure 7A:
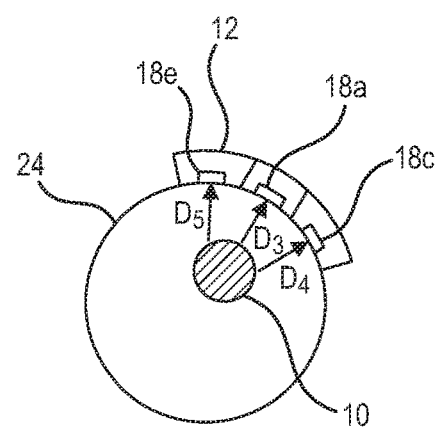
FIG. 7A illustrates a schematic cross-sectional view of the patch shown in FIG. 7.

FIGS. 7 and 7a illustrate an example embodiment in which a patch 12, similar to the patch 12 shown in FIGS. 6 and 6a, is positioned such that the Z axis of the patch 12 extends substantially parallel to the longitudinal axis 44 of the vessel 10, but is spaced laterally from the axis 44 in a direction substantially transverse to the axis 44. Additionally, as in FIGS. 6 and 6a, the X axis of the patch 12 extends substantially transverse to the longitudinal axis 44 of the vessel 10. In such an embodiment, the distance D4 between the sensor 18c and the vessel 10 may be greater than the distance D5 between the sensor 18e and the vessel 10. As a result, assuming that the thermal resistance of the body tissue between the vessel 10 and the patch 12 is relatively constant, a skin surface temperature measured by the sensor 18c may be less than a corresponding skin surface temperature measured by the sensor 18e. Further, respective differences between skin surface temperatures measured by the sensors 18c, 18e, and a corresponding skin surface temperature measured by sensor 18a may be indicative of the orientation of the patch 12 and/or the sensors 18a, 18c, 18e relative to the blood vessel 10.

For example, the controller 20 and/or other components of the system 100 may determine the difference between skin surface temperatures measured by the sensors 18a and 18c, and may also determine the difference between skin surface temperatures measured by the sensors 18a and 18e. The controller 20 and/or other components of the system 100 may determine the orientation of the sensors 18a, 18c, 18e and/or of the patch 12 relative to the blood vessel 10 based on such differences. The difference in skin surface temperatures determined by the sensors 18c, 18e and/or the actual measured temperatures may also be used by the controller 20 to determine the orientations described herein. In such examples, the determined orientation of the patch 12 may also be based at least in part, the thermal resistance of a skin layer and/or body tissue of the limb 22.

Figure 8:
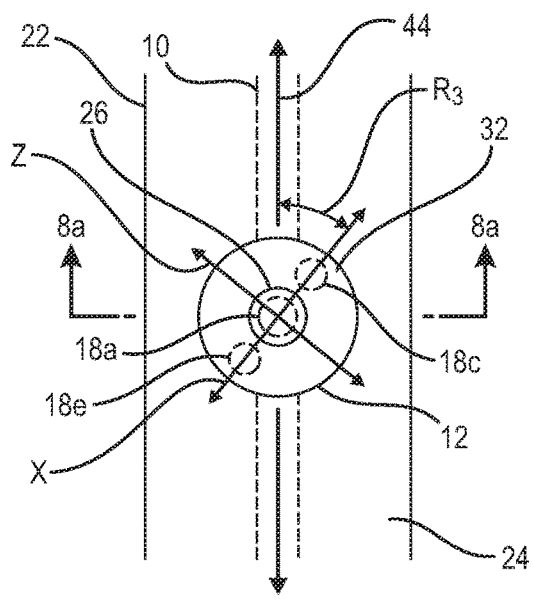
FIG. 8 illustrates an example patch disposed on a skin surface of a patient according to a further embodiment of the present disclosure.
Figure 8A:
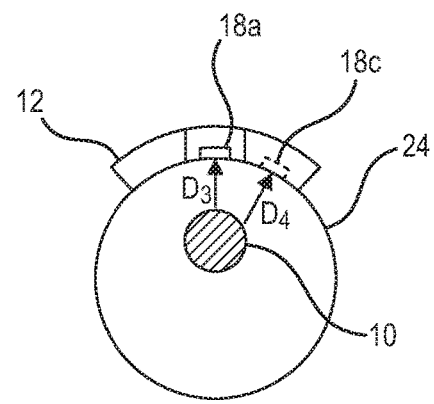
FIG. 8A illustrates a schematic cross-sectional view of the patch shown in FIG. 8.

FIGS. 8 and 8a illustrate an example embodiment in which a patch 12, similar to the patch 12 shown in FIGS. 6 and 6a, is positioned such that the Z axis of the patch 12 is positioned at a radial angle R3 relative to the longitudinal axis 44 of the vessel 10. In such an embodiment, depending on the value of the radial angle R3, the distance D4 between the sensor 18c and the vessel 10 may be greater than, less than, or equal to the distance D5 between the sensor 18e and the vessel 10. For ease of description, R3 will be described as having a value of 45 degrees such that the distance D4 is equal to the distance D5. As a result, assuming that the thermal resistance of the body tissue between the vessel 10 and the patch 12 is relatively constant, skin surface temperatures measured by the sensors 18c, 18e may be substantially equal. Further, as noted above with respect to FIGS. 6 and 6a, a difference between a skin surface temperature measured by one or both of the sensors 18c, 18e, and a corresponding skin surface temperature measured by sensor 18a may be indicative of the orientation of the patch 12 and/or the sensors 18a, 18c, 18e relative to the blood vessel 10.

For example, the controller 20 and/or other components of the system 100 may determine the value of the radial angle R3 based at least in part on differences between skin surface temperatures measured by the sensors 18c and 18a (e.g., a first difference), 18e and 18a (e.g., a second difference), and/or 18e and 18c (e.g., a third difference). In such examples, the determined orientation of the patch 12 may also be based at least in part, on the thermal resistance of a skin layer and/or body tissue of the limb 22. Further, in such examples, temperature measurements obtained using one or more of the sensors 18d, 18f, 18h described herein may also be used by the controller 20 and/or other components of the system 100 to determine the value of the radial angle R3.

Figure 9:
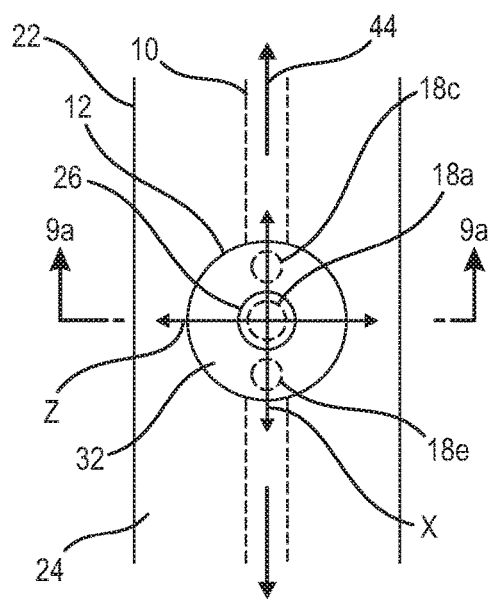
FIG. 9 illustrates an example patch disposed on a skin surface of a patient according to still another example embodiment of the present disclosure.
Figure 9A:
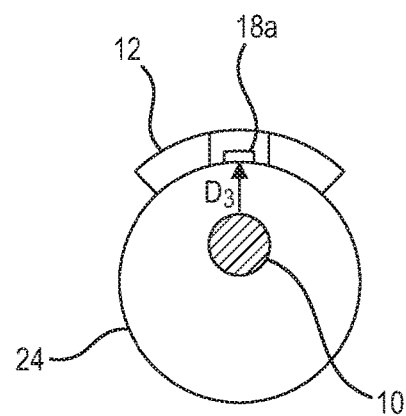
FIG. 9A illustrates a schematic cross-sectional view of the patch shown in FIG. 9.

FIGS. 9 and 9a illustrate an example embodiment in which a patch 12, similar to the patch 12 shown in FIGS. 6 and 6a, is positioned such that the X axis of the patch 12 is aligned with and extends substantially parallel to the longitudinal axis 44 of the vessel 10. Additionally, the Z axis of the patch 12 extends substantially transverse to the longitudinal axis 44 of the vessel 10. In such examples, the distances D3, D4, D5 between the respective sensors 18a, 18c, 18e and the vessel 10 may be substantially equal. As a result, assuming that the thermal resistance of the body tissue between the vessel 10 and the patch 12 is relatively constant, skin surface temperatures measured by the sensors 18c, 18e may be substantially equal. Further, a difference between a skin surface temperature measured by one or both of the sensors 18c, 18e, and a corresponding skin surface temperature measured by sensor 18a may be indicative of the orientation of the patch 12 and/or the sensors 18a, 18c, 18e relative to the blood vessel 10.

For example, if the difference between a skin surface temperature measured by one or both of the sensors 18c, 18e and a corresponding skin surface temperature measured by the sensor 18a is greater than a predetermined threshold temperature, the controller 20 and/or other components of the system 100 may determine that the X axis of the patch 12, along which the sensors 18a, 18c, 18e are disposed, extends substantially parallel to and is substantially aligned with the longitudinal axis 44 of the vessel 10. In such examples, the determined orientation of the patch 12 may also be based at least in part, the thermal resistance of a skin layer and/or body tissue of the limb 22. Further, in such examples, temperature measurements obtained using one or more of the sensors 18d, 18f, 18h described herein may also be used by the controller 20 and/or other components of the system 100 to determine the orientation of the patch 12 illustrated in FIGS. 9 and 9a.

Figure 10:
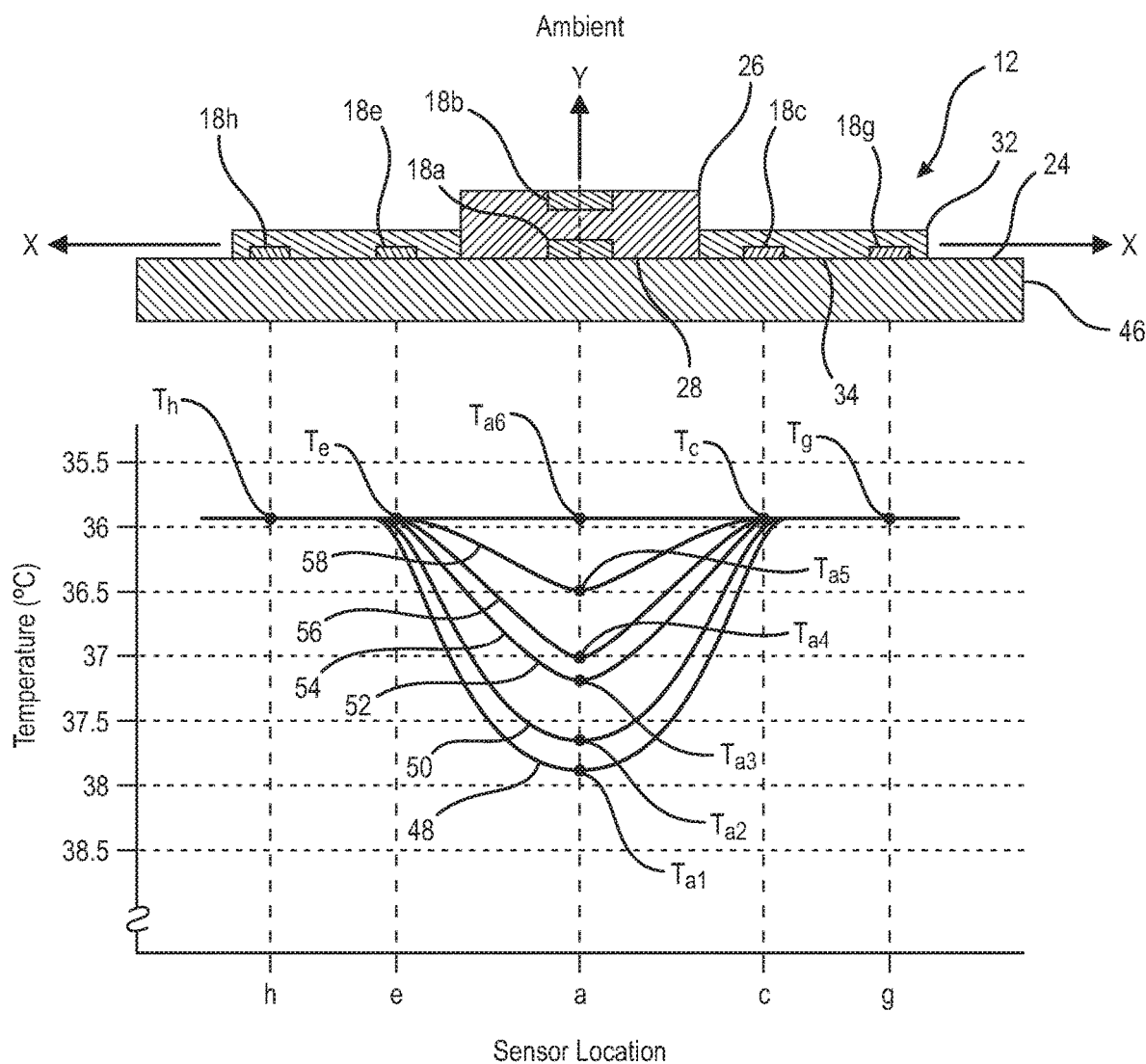
FIG. 10 illustrates a plot of temperature versus sensor location according to an example embodiment of the present disclosure.

FIG. 10 illustrates a schematic cross-sectional view of an example patch 12 disposed on a skin surface 24, and a corresponding temperature vs. sensor location plot. The example patch 12 shown in FIG. 10 includes sensors 18g, 18c, 18e, and 18h disposed substantially along the longitudinal X axis of patch 12 within the second portion 32. The example patch 12 also includes sensor 18a disposed along the X axis within the first portion 26, and sensor 18b disposed along the Y axis in the first portion 26. In the embodiment of FIG. 10, the sensor 18b is exposed to conditions of an ambient environment while the sensor 18a is substantially thermally isolated (e.g., substantially insulated) from the ambient condition by the first portion 26. Additionally, in the example embodiment of FIG. 10, while the sensors 18g, 18c, 18e, and 18h may be embedded substantially within the material of the second portion 32, such material may have a thermal resistance that is significantly less than a corresponding thermal resistance of the material making up the first portion 26. In such embodiments, conditions of the ambient environment (e.g., an ambient temperature) may have a larger effect on skin surface temperature determinations made by one or more of the sensors 18g, 18c, 18e, 18h than, for example, the sensor 18a.

As shown in FIG. 10, the patch 12 may be disposed on the skin surface 24 such that the first and third surfaces 28, 34 of the first and second portions 26, 32 are in contact with the skin surface 24, and the sensors 18g, 18c, 18a, 18e, 18h are positioned to determine respective skin surface temperatures at corresponding longitudinal locations along the skin surface 24. Such locations g, c, a, e, and h are identified along the "sensor location" axis of the plot shown in FIG. 10 and correspond to the longitudinal location of the respective sensors 18g, 18c, 18a, 18e, 18h on the skin surface 24.

Further, based at least in part on variations in the thermal resistance of a skin layer 46 corresponding to the skin surface 24, skin surface temperatures determined by the sensors 18g, 18c, 18a, 18e, 18h may vary. These variations in the thermal resistance of the skin layer 46 may be caused by changes in ambient conditions and/or by physical activity, health, illness, disease state, or other physical conditions of the subject 14. For example, subjecting the skin layer 46 to a decrease in ambient temperature may result in corresponding increase in thermal resistance of the skin layer 46 caused by closing of capillaries and/or other blood vessels. Alternatively, subjecting the skin layer 46 to an increase in ambient temperature may result in a corresponding decrease in thermal resistance of the skin layer 46 caused by opening of capillaries and/or other blood vessels. In example embodiments of the present disclosure, the variable or otherwise dynamic thermal resistance of the skin layer 46 on which the patch 12 is disposed may determine the degree to which temperatures determined by the sensors 18g, 18c, 18a, 18e, 18h should be adjusted or corrected, such as by a multiplier, a weight, and/or by another correction factor, when determining a core temperature of the subject 14. Alternatively, the variable thermal resistance of the skin layer 46 may determine the degree to which the ultimate core temperature of the subject 14 should be adjusted or corrected.

With continued reference to FIG. 10, the temperature Tg corresponds to a skin surface temperature measured and/or otherwise determined by the sensor 18g, the temperature Tc corresponds to a skin surface temperature measured and/or otherwise determined by the sensor 18c, the temperatures Ta corresponds to skin surface temperatures measured and/or otherwise determined by the sensor 18a, the temperature Te corresponds to a skin surface temperature measured and/or otherwise determined by the sensor 18e, and the temperature Th corresponds to a skin surface temperature measured and/or otherwise determined by the sensor 18h. In such an example embodiment, the sensors 18g, 18c, 18e, and 18h may be substantially thermally isolated from the material of the first portion 26 and, as a result, the skin surface temperatures determined by the sensor 18g may be substantially equal to the skin surface temperature determined by the sensor 18h, and the skin surface temperatures determined by the sensor 18c may be substantially equal to the skin surface temperature determined by the sensor 18e. Further, in some examples, skin surface temperatures determined by each of the sensors 18g, 18c, 18e, and 18h may be substantially equal.

The skin surface temperatures determined by the sensor 18a may, however, differ from one or more of the skin surface temperatures determined by the sensors 18g, 18c, 18e, 18h based at least in part on variations in the thermal resistance of the skin layer 46 and/or on the insulative effect of the material of the first portion 26 on the sensor 18a. For example, the temperature curve 48 illustrates a condition in which the subject 14 is below the interthreshold zone and is hypothermic. Such conditions may cause significant vasoconstriction and/or shivering in order to maintain a core body temperature of the subject 14. In such examples, the skin layer 46 may have a relatively high thermal resistance, and a difference between the temperature Ta1 and, for example, one or more of the temperatures Tg, Tc, Te, and Th may be relatively high due to relatively low perfusion levels in the skin layer 46 as well as the insulative effect of the material of the first portion 26 on the sensor 18a.

The temperature curve 50 illustrates a condition in which the subject 14 is below the interthreshold zone and is normothermic. Such conditions may cause increased vasoconstriction in order to maintain a core body temperature of the subject 14. In such examples, the skin layer 46 may still have a relatively high thermal resistance, and a difference between the temperature Ta1 and, for example, one or more of the temperatures Tg, Tc, Te, and Th may be relatively high due to relatively low perfusion levels in the skin layer 46 as well as the insulative effect of the material of the first portion 26 on the sensor 18a.

Further, the temperature curve 52 illustrates a condition in which the subject 14 is in the interthreshold zone and is normothermic. Such conditions may be characterized by relatively normal homeostatic thermal regulation and, as a result, the skin layer 46 may have a relatively moderate thermal resistance that is higher than the thermal resistances described above with respect to curves 48 and 50. In such conditions, a difference between the temperature Ta1 and, for example, one or more of the temperatures Tg, Tc, Te, and Th may be lower than the differences described above with respect to curves 48 and 50 due to increased perfusion levels in the skin layer 46 as well as the Insulative effect of the material of the first portion 26 on the sensor 18a.

The temperature curve 54 illustrates a condition in which the subject 14 is febrile. In such conditions, the body of the subject 14 may be actively attempting to increase core temperature and, as a result, the skin layer 46 may have a relatively low thermal resistance as compared to the thermal resistances described above with respect to curves 48, 50, and 52. In such conditions, a difference between the temperature Ta1 and, for example, one or more of the temperatures Tg, Tc, Te, and Th may be lower than the differences described above with respect to curves 48, 50, and 52 due to elevated perfusion levels in the skin layer 46 as well as the insulative effect of the material of the first portion 26 on the sensor 18a.

The temperature curve 56 illustrates a condition in which the subject 14 is above the interthreshold zone and is normothermic. Such conditions may cause significant vasodilation and/or sweating in order to reduce a core body temperature of the subject 14. As a result, the skin layer 46 may have a relatively low thermal resistance as compared to the thermal resistances described above with respect to curves 48, 50, and 52. In such conditions, a difference between the temperature Ta1 and, for example, one or more of the temperatures Tg, Tc, Te, and Th may be lower than the differences described above with respect to curves 48, 50, and 52 due to significantly elevated perfusion levels in the skin layer 46 as well as the insulative effect of the material of the first portion 26 on the sensor 18a.

Further, the temperature curve 58 illustrates a condition in which the subject 14 is above the interthreshold zone and is hypothermic. Such conditions may cause maximized levels of vasodilation and/or sweating in order to reduce a core body temperature of the subject 14. As a result, the skin layer 46 may have a minimized thermal resistance and the difference between the temperature Ta1 and, for example, one or more of the temperatures Tg, Tc, Te, and Th may be negligible due to such extreme perfusion levels in the skin layer 46. Further, in such conditions the insulative effect of the material of the first portion 26 on the sensor 18a may be negligible.

In any of the examples described herein, the gradient or difference between the temperature Ta1 and one or more of the temperatures Tg, Tc, Te, Th may be indicative of, among other things, the dynamic thermal resistance of the skin layer 46 and/or the insulative effect of the material of the first portion 26 on the sensor 18a. In some examples, one or more such differences may be used as inputs, such as by the controller 20, to determine a value of such a variable thermal resistance of the skin layer 46 for the purpose of determining the core temperature of the subject 14. In further examples, an example patch 12 and/or the controller 20 may be configured to employ one or more algorithms to determine a temperature of the subject 14, and one or more such algorithms may be selected based at least partly on the measurement site at which the patch 12 is disposed. In such examples, the gradient or difference between the temperature Ta1 and one or more of the temperatures Tg, Tc, Te, Th may be weighted differently in such algorithms depending on the location of such a measurement site. For example, such a difference may be given a first weigh if the patch 12 is disposed on a skin surface 24 associated with the clavicle, and such a difference may be given a second weight different from the first weight if the patch 12 is disposed on a skin surface 24 associated with the axilla.

Additionally or alternatively, one or more such differences may be used as inputs, such as by the controller 20, to determine a weight, a multiplier, and/or other correction factor associated with an estimated thermal resistance of the skin layer 46 used in determining the core temperature of the subject 14. In such examples, the thermal resistance of at least one of the material of the first portion 26 and the material of the second portion 32 may also be used as an input in determining the variable thermal resistance of the skin layer 46. In still another example, a calibration factor, determined as a result of a dynamic characterization of one or both portions 26, 32 of the patch 12 during the production of the patch 12, may be used as an input in determining the variable thermal resistance of the skin layer 46.

Figure 11:
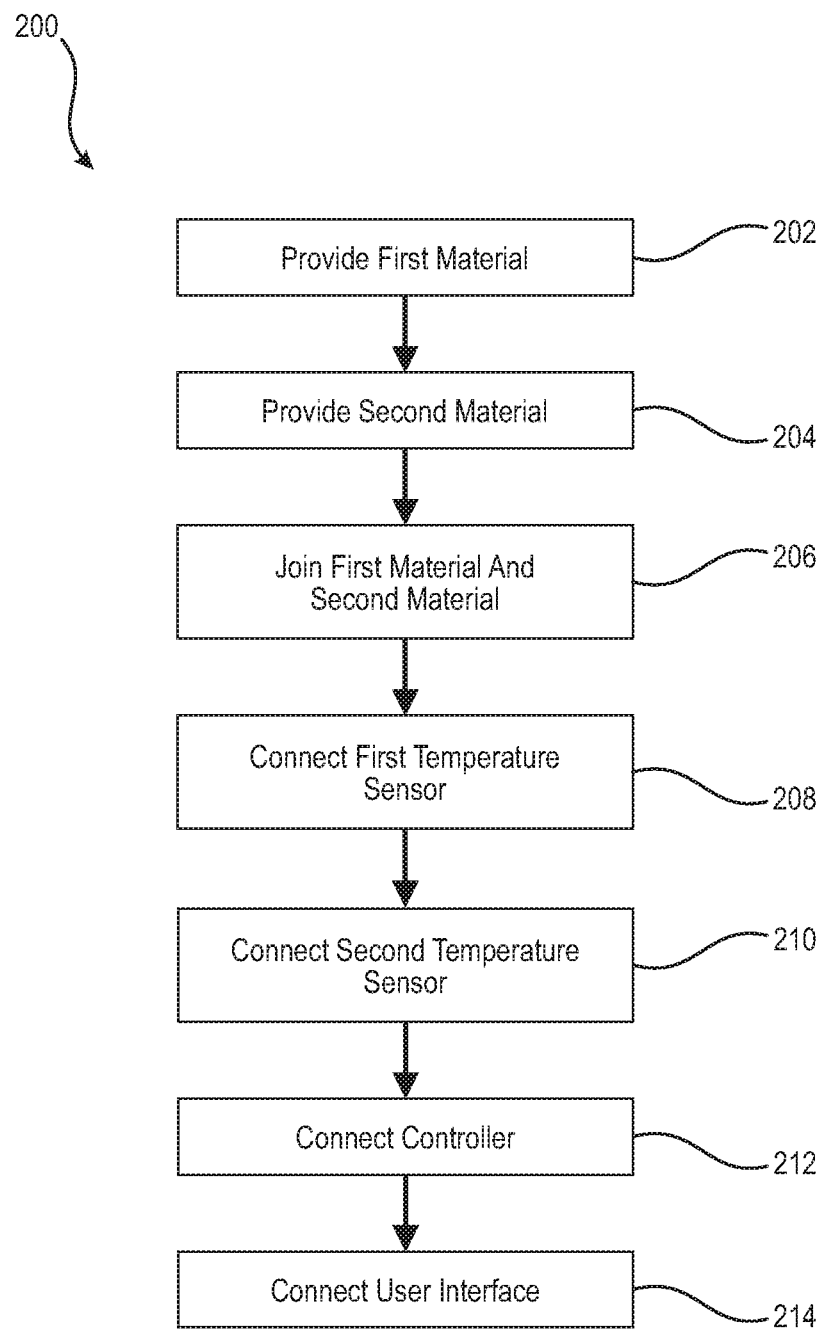
FIG. 11 shows a flowchart illustrating an example method of the present disclosure.

FIG. 11 shows a flowchart 200 illustrating an example method of the present disclosure. Such a method may be, for example, a method of manufacturing an example system, such as the system 100 described herein. As shown in FIG. 11, at step: 202 such a method may include providing a first material, such as any of the insulative materials described above. In such examples, the first material may have a first thermal resistance, and the first material may include a first surface and a second surface opposite the first surface. For example, the first material provided at step: 202 may make up the first portion 26 of the patch 12, and the first surface 28 may be removably attachable to the skin surface 24 of the subject 14. At step: 204 the method may include providing a second material different from the first material and having a second thermal resistance that is less than the first thermal resistance associated with the first material. For example, the second material provided at step: 204 may make up the second portion 32 of the patch 12, and may include the third and fourth surfaces 34, 36. In such examples, the third surface 34 may be removably attachable to the skin surface 24.

At step: 206 the method may include joining the first material and the second material to form a wearable patch 12 such that the third surface 34 extends substantially coplanar with the first surface 28. As noted above, the first and second portions 26, 32 may be formed using any known manufacturing process such as molding, extrusion, pressing, or other process. Additionally, at step: 206 the first and second portions 26, 32 may be joined and/or otherwise connected via any of these processes or by adhesion, welding, heat sealing, or other known processes. Such an example method may also include joining and/or otherwise connecting a base layer 38 to at least one of the first and second portions 26, 32 in a similar manner.

At step: 208 the method may include connecting a first temperature sensor to at least a portion of the patch 12. For example, at step: 208 the method may include embedding a first temperature sensor 18a substantially within the first material of the first portion 26 such that the first temperature sensor 18a is disposed adjacent to the first surface 28. Similarly, at step: 210 the method may include connecting at least one additional temperature sensor 18 to at least a portion of the patch 12. For example, at step: 210 the method may include embedding a second temperature sensor 18c substantially within the second material such that the second temperature sensor 18c is disposed adjacent to the third surface 34 and the second temperature sensor 18c is substantially thermally isolated from the first portion 26. It is understood that a system manufactured according to the method described above with respect to FIG. 11 may be configured such that when the first and third surfaces 28, 34 are disposed on the skin surface 24 of the subject 14, a difference between a first temperature of the skin surface 24 determined by the first temperature sensor 18a and a second temperature of the skin surface 24 determined by the second temperature sensor 18c may be indicative of a position of at least one of the first and second temperature sensors 18a, 18c relative to a blood vessel 10 disposed within the limb 22.

In some examples, the first and second temperature sensors 18 may be disposed along a first longitudinal axis of the patch 12, such as the X axis, and the first and second surfaces 28, 34 may extend substantially parallel to the first longitudinal axis. In such examples, the method may also include embedding a third temperature sensor substantially within the second material of the second portion 32 such that the third temperature sensor is disposed adjacent to the third surface 34. As shown in at least FIGS. 2-5, in such examples the method may include embedding the third temperature sensor such that the sensor is disposed along the first longitudinal axis. For example, the third temperature sensor may be disposed further radially outward from a transverse axis of the patch 12, such as the Y axis, than the second temperature sensor. In other examples, however, the third temperature sensor may be disposed along a second longitudinal axis of the patch 12, such as the Z axis, substantially perpendicular to the first longitudinal axis, and the first and third surfaces 28, 34 may extend substantially parallel to the second longitudinal axis.

In still further examples, the method may include embedding a third temperature sensor substantially within the first material of the first portion 26 such that the third temperature sensor is disposed adjacent to the second surface 30. As shown in at least FIGS. 2-5, in such examples the method may include embedding the third temperature sensor such that the sensor is disposed along a second axis of the patch 12, such as the Y axis, extending substantially perpendicular from the first longitudinal axis, the first and second surfaces 28, 30 being substantially perpendicular to the second axis.

At step: 212 the method may also include connecting, such as operably connecting, a controller 20 to the first and second temperature sensors 18a, 18c. It is understood that such an operable connection may be made by one or more leads, wires, and/or other physical connection components between the controller 20 and the first and second temperature sensors 18a, 18c. Alternatively, such an operable connection may be made wirelessly. As described above, the controller 20 may be configured to determine a core temperature of the subject 14 based at least partly on the first and second skin surface temperatures measured by the first and second temperature sensors 18a, 18c, and a correction factor. In such examples, the correction factor may be determined based on the difference between a first temperature of the skin surface 24 (determined by the first temperature sensor 18a) and a second temperature of the skin surface 24 (determined by the second temperature sensor 18c). Additionally or alternatively, such a correction factor may be determined based on at least one of the thermal resistance of the first material and the thermal resistance of the second material.

At step: 214, the method may further include connecting, such as operably connecting, a user interface 16 with at least one of the controller 20, the first temperature sensor 18a, and the second temperature sensor 18c. It is understood that such an operable connection may be made by one or more leads, wires, and/or other physical connection components. Alternatively, such an operable connection may be made wirelessly. It is also understood that a patch 12 and/or system 100 manufactured according to the example method illustrated by the flowchart 200 may be configured to determine one or more core temperatures of the subject 14 based on any of the core temperature determination methods, or aspects thereof, described herein.

Figure 12:
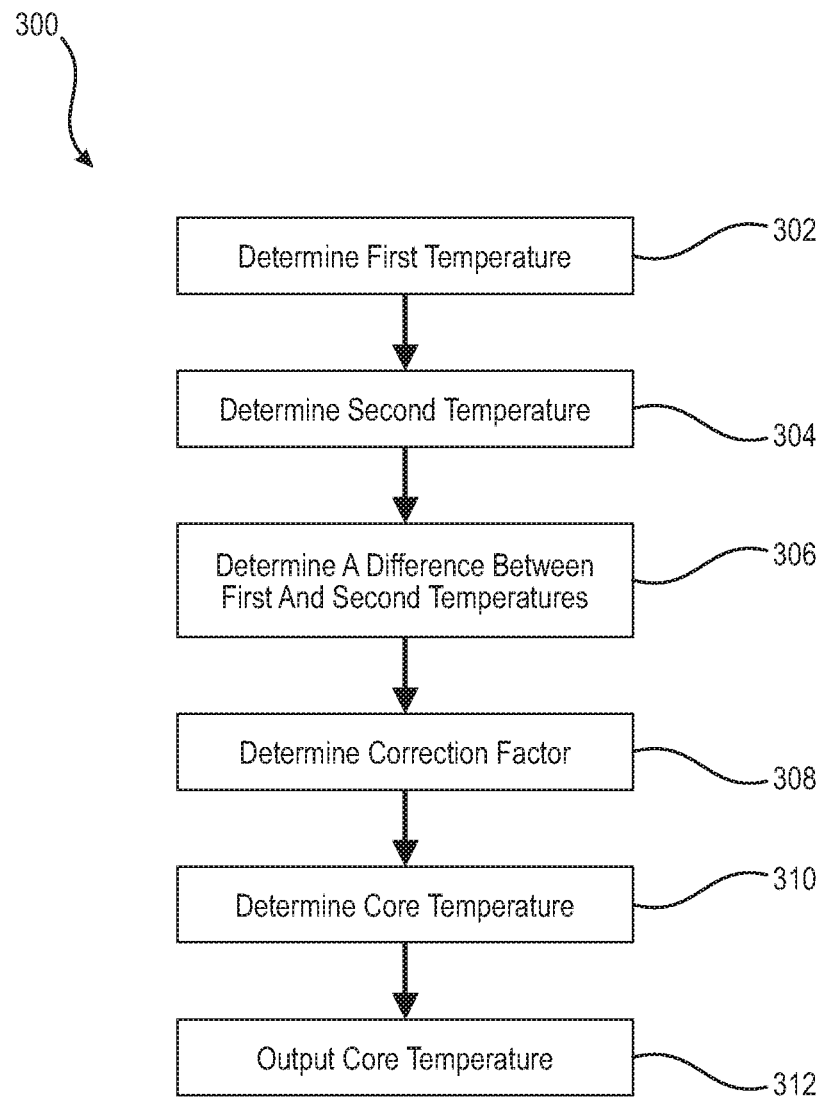
FIG. 12 shows a flowchart illustrating another example method of the present disclosure.

FIG. 12 shows a flowchart 300 illustrating another example method of the present disclosure. Such a method may be, for example, a method of determining a core temperature of the subject 14. As shown in FIG. 12, at step: 302 such a method may include determining a first temperature of a skin surface 24 of the subject 14 with a first temperature sensor 18 of a wearable patch 12. In some examples, the skin surface 24 may comprise a skin surface of a limb 22 of the subject 14. Additionally, in some examples, the patch 12 may be similar to and/or the same as one or more of the patches 12 described above with respect to FIGS. 1-11. For example, such an example patch 12 may include a first portion 26 made from a first insulative material, and including a first surface 28 and a second surface 30 opposite the first surface 28. Additionally, in such example embodiments, the first temperature sensor may be embedded substantially within the first portion 26 adjacent to the first surface 28. Moreover, the patch 12 may include a second portion 32 made from a second material different than the first material. In such examples, the second portion 32 may include a third surface 34 extending substantially coplanar with the first surface 28 of the first portion 26. Additionally, the first material of the first portion 26 may have a first thermal resistance, and the second material of the second portion 32 may have a second thermal resistance less than the first thermal resistance. For example, while the first material of the first portion 26 may be a thermal insulator, the second material of the second portion 32 may provide a level of thermal insulation that is negligible.

At step: 304 the method may also include determining a second temperature of the skin surface 24 with the second temperature sensor 18 of the patch 12. In such examples, the second temperature may be determined when the patch 12 is disposed on and/or removably attached to the skin surface 24. Additionally, the second temperature sensor 18 may be embedded substantially within the second portion 32 of the patch 12 adjacent to the third surface 34. At step: 306 the method may include determining a difference between the first and second temperatures of the skin surface 24. As described above with respect to at least FIGS. 6-9A, in some examples the difference may be indicative of a position and/or an orientation of the patch 12 relative to a blood vessel 10 disposed within the limb 22. Further, as described above with respect to at least FIG. 10, such a difference may be used as an input in determining a correction factor and/or a dynamic thermal resistance of a skin layer 46 associated with the skin surface 24. Indeed, at step: 308 the method may include determining such a correction factor and/or such a thermal resistance based on the difference between the first and second temperatures of the skin surface 24.

At step: 310 the method may also include determining a core temperature of the subject 14 based on at least one of the first temperature, the second temperature, the orientation of the patch 12, the correction factor, and the thermal resistance of the skin layer 46. For example, at step: 310 the controller 20 may use the first and second temperatures, and/or the correction factor as inputs into one or more core temperature determination algorithms. Additionally, at step: 312 the method may include outputting the core temperature determined at step: 310. For example, at step: 312 the controller 20 may display and/or otherwise provide the determined core temperature via a display and/or other component of user Interface 16.

In the various embodiments described herein, a correction factor may be calculated and/or otherwise determined based on differences and/or gradients between the various skin surface temperatures described above. For example, the amount of heat flow (stray conduction) caused by blood moving through the skin layer 46 proximate the first and third surfaces 28, 34 can be estimated using the skin surface temperatures measured by one or more of the sensors 18g, 18c, 18a, 18e, 18h. In such examples, equation [1] below can be used by the controller 20 to calculate a core temperature of the subject 14:

$$T_{core} = T_1 + R(T_1 - T_2) + CF. \quad [1]$$

In the above equation, $T_1$ may be a skin surface temperature measured by the temperature sensor 18a, $T_2$ may be a skin surface temperature measured by the temperature sensor 18c, and R may be a dynamic thermal resistance of the skin layer 46 determined by the controller 20. Additionally, the correction factor "CF" may compensate for heat flow (stray conduction) caused by blood flow moving through the skin layer 46, and the correction factor CF may be calculated according to the following equation:

$$CF = SC_t(\Delta T_{max})(T_1 - T_2). \qquad [2]$$

In the above equation, "$SC_t$" may be an empirically derived constant converting the cross-patch temperature gradient to a temperature adjustment due to stray conduction effects. In addition, "$\Delta T_{max}$" may be the difference between the lowest sensed temperature and the highest sensed temperature among the sensors 18 included in the patch 12.

As noted above, in any of the example embodiments described herein, the first and second temperatures of the skin surface 24 may be determined substantially simultaneously by the first and second temperature sensors 18, respectively. Additionally, any of the methods described herein may include determining a plurality of sequential core temperatures at any desired time interval. In such examples, the controller 20, and/or other components of the system 100 may compare one or more of the sequential core temperatures to a predetermined threshold temperature. In such examples, the controller 20, and/or the user interface 16 may trigger an audible, visual, and/or other alarm in response to such a comparison. Additionally, such example methods may Include determining a core temperature change rate based on the plurality of sequential core temperature determinations. In such examples, the controller 20 may compare such a core temperature change rate to a predetermined threshold change rate. Additionally, the controller 20, and/or the user interface 16 trigger an audible, visual, and/or other alarm in response to such a comparison.

In any of the example embodiments described herein, the patch 12 may include at least one temperature sensor 18b embedded substantially within the first portion 26 adjacent to the second surface. As noted above, such a temperature sensor 18b may be positioned, and/or otherwise configured to determine a temperature of the ambient environment in which the patch 12 is being used. Accordingly, in such examples, temperature sensor 18b may determine an ambient temperature when the patch 12 is disposed on the skin surface 24, and in such examples, the controller 20 may determine the core temperature based at least in part on the ambient temperature determined by the temperature sensor 18b as well as one or more of the skin surface temperatures determined by the additional temperature sensors 18 of the patch 12. Determining the core temperature of the subject 14 based at least partly on a determined ambient temperature may increase the accuracy of the overall core temperature determination.

Moreover, as noted above, any of the example embodiments described herein may include determining a value of a variable and/or otherwise dynamic thermal resistance of the layer of skin 46 associated with the skin surface 24 on which the patch 12 is disposed. As described with respect to at least FIG. 10, the thermal resistance of such a skin layer 46 may change over time depending upon ambient conditions, and/or one or more physical conditions of the subject 14. In example embodiments, the controller 20 may utilize actual skin surface temperatures determined by one or more of the sensors 18, and/or differences between such skin surface temperatures as inputs into one or more algorithms utilized to determine the thermal resistance of the skin layer 46. Additionally, and/or alternatively, the controller 20 may utilize such actual skin surface temperatures or differences between such skin surface temperatures as inputs into one or more lookup tables, charts, neural networks, and/or other controller components in determining the thermal resistance of the skin layer 46. By determining the value of such a dynamic thermal resistance of the skin layer 46, as opposed to using an assumed constant value, the accuracy of the core temperature determinations described herein may be further improved.

The invention has been described in detail with particular reference to a presently preferred embodiment, but it will be understood that variations and modifications can be effected within the spirit and scope of the invention. The presently disclosed embodiments are, therefore, considered in all respects to be illustrative and not restrictive. The scope of the invention is indicated by the appended claims, and all changes that come within the meaning and range of equivalents thereof are intended to be embraced therein.

The invention claimed is:

1. A wearable patch, comprising:
a first portion comprising a first insulative material, the first portion including a first surface, a second surface opposite the first surface, and a central axis extending substantially perpendicular to the first surface;
a second portion comprising a second material different from the first material, the second portion including a third surface extending substantially coplanar with the first surface, and a fourth surface opposite the third surface;
a first temperature sensor embedded substantially within the first material of the first portion and disposed adjacent to the first surface; and
a second temperature sensor embedded substantially within the second material of the second portion and disposed adjacent to the third surface, wherein:
the first portion comprises a first thickness extending from the first surface to the second surface,
the second portion comprises a second thickness extending from the third surface to the fourth surface, the second thickness being less than the first thickness,
the second portion surrounds a radially outermost perimeter of the first portion,
a radially outermost perimeter of the second portion forms a radially outermost perimeter of the patch,
when the patch is disposed on a skin surface of a patient such that the first surface is disposed closer to the skin surface than the second surface, a difference between a first temperature of the skin surface determined by the first temperature sensor and a second temperature of the skin surface determined by the second temperature sensor is indicative of an orientation of the patch relative to a blood vessel disposed proximate the skin surface, and
the first and second temperature sensors are operably connected to a controller configured to receive signals from the first and second temperature sensors indicative of the first and second temperatures, the controller being programmed to:
determine a rotational orientation of the patch, about the central axis and relative to the blood vessel, based at least in part on the first and second temperatures, and
generate an alarm, based on the rotational orientation of the patch, indicating that the rotational orientation of the patch should be changed.

2. The patch of claim 1, wherein the first material has a first thermal resistance and the second material has a second thermal resistance less than the first thermal resistance.

3. The patch of claim 1, wherein the second temperature sensor is spaced from the first temperature sensor such that the second temperature sensor is substantially thermally isolated from the first portion and the second temperature determined by the second temperature sensor is substantially unaffected by the first material.

4. The patch of claim 1, wherein the first and second temperature sensors are disposed along a first longitudinal axis of the patch extending substantially perpendicular to the central axis, and the first and second surfaces extend substantially parallel to the first longitudinal axis.

5. The patch of claim 4, wherein the patch includes a third temperature sensor embedded substantially within the second material of the second portion and disposed adjacent to the third surface along the first longitudinal axis.

6. The patch of claim 4, wherein the patch includes a third temperature sensor embedded substantially within the second material of the second portion and disposed adjacent to the third surface, the third temperature sensor being disposed along a second longitudinal axis of the patch substantially perpendicular to the first longitudinal axis, the first and third surfaces extending substantially parallel to the second longitudinal axis.

7. The patch of claim 4, wherein the patch includes a third temperature sensor embedded substantially within the first material of the first portion and disposed adjacent to the second surface, the third temperature sensor being disposed along the central axis of the patch, the first and second surfaces extending substantially perpendicular to the central axis.

8. The patch of claim 1, the controller being configured to determine a dynamic thermal resistance of a skin layer corresponding to the skin surface using the difference as an input, and to determine a patient temperature based on the determined thermal resistance.

9. The patch of claim 1, the controller being configured to determine a correction factor based on the difference, and to determine a patient temperature based on the first and second temperatures, and the correction factor.

10. The patch of claim 9, wherein the correction factor is indicative of a position of at least one of the first temperature sensor and the second temperature sensor relative to the blood vessel.

11. The patch of claim 1, wherein the first and third surfaces extend along a longitudinal axis of the patch extending substantially perpendicular to the central axis.

12. The patch of claim 1, wherein the controller is configured to:
  determine a correction factor based at least in part on the orientation of the patch, and
  determine a patient temperature based on the first and second temperatures, and the correction factor.

13. The patch of claim 1, further including a base layer connected to the first surface and the third surface.

14. A computer-readable storage device containing instructions that, when executed by a controller, cause the controller to perform operations, comprising:
  determining a first temperature, of a skin surface of a patient, with a first temperature sensor of a wearable patch, wherein the first temperature is determined when the patch is disposed on the skin surface, and the skin surface comprises a skin surface of a patient, the patch including:
    a first portion comprising a first insulative material, the first portion including a first surface, a second surface opposite the first surface, and a central axis extending substantially perpendicular to the first surface, the first temperature sensor being embedded substantially within the first portion adjacent to the first surface, and
    a second portion comprising a second material different from the first material, the second portion including a third surface extending substantially coplanar with the first surface, and a fourth surface opposite the third surface, the first material having a first thermal resistance, and the second material having a second thermal resistance less than the first thermal resistance, wherein
      the first portion comprises a first thickness extending from the first surface to the second surface,
      the second portion comprises a second thickness extending from the third surface to the fourth surface, the second thickness being less than the first thickness,
      the second portion surrounds a radially outermost perimeter of the first portion, and
      a radially outermost perimeter of the second portion forms a radially outermost perimeter of the patch;
  determining a second temperature of the skin surface with a second temperature sensor of the patch, wherein the second temperature is determined when the patch is disposed on the skin surface, and the second temperature sensor is embedded substantially within the second portion adjacent to the third surface;
  determining a difference between the first and second temperatures, wherein the difference is indicative of an orientation of the patch relative to a blood vessel disposed proximate the skin surface;
  determining a correction factor based on the difference;
  determining a patient temperature based on the first temperature, the second temperature, and the correction factor;
  determining a rotational orientation of the patch, about the central axis and relative to the blood vessel, based at least in part on the first and second temperatures; and
  generating an alarm, based on the rotational orientation of the patch, indicating that the rotational orientation of the patch should be changed.

15. The computer-readable storage device of claim 14, wherein the patch further includes a third temperature sensor embedded substantially within the first portion adjacent to the second surface, the operations further comprising:
  determining a third temperature with the third temperature sensor when the when the patch is disposed on the skin surface, and
  determining the patient temperature based on the third temperature.

16. The computer-readable storage device of claim 14, the operations further comprising determining a dynamic thermal resistance of a skin layer corresponding to the skin surface using the difference as an input, and determining the patient temperature based on the determined thermal resistance.

17. The computer-readable storage device of claim 14, wherein:
  a radial distance between the radially outermost perimeter of the first portion and the second temperature sensor is used as an input in determining the patient temperature, and the radial distance positions the second sensor at a location of the second portion relative to the first portion at which the second temperature sensor is substantially thermally isolated from the first portion of the patch.

18. The computer-readable storage device of claim 17, wherein the correction factor is determined based at least in part on the radial distance between the radially outermost perimeter of the first portion and the second temperature sensor.

19. A method of manufacturing a system, comprising:

providing a first insulative material having a first thermal resistance, the first material including a first surface, a second surface opposite the first surface, a central axis extending substantially perpendicular to the first surface, and a first thickness extending from the first surface to the second surface;

providing a second material different from the first material and having a second thermal resistance less than the first thermal resistance;

joining the first material and the second material to form a wearable patch such that a third surface of the second material extends substantially coplanar with the first surface, the second material including a fourth surface opposite the third surface, and a second thickness extending from the third surface to the fourth surface, the second thickness being less than the first thickness, wherein:

the second material surrounds a radially outermost perimeter of the first material, and a radially outermost perimeter of the second material forms a radially outermost perimeter of the patch;

embedding a first temperature sensor substantially within the first material such that the first temperature sensor is disposed adjacent to the first surface;

embedding a second temperature sensor substantially within the second material such that the second temperature sensor is disposed adjacent to the third surface and the second temperature sensor is substantially thermally isolated from the first material and operably connecting a controller to the first and second temperature sensors, the controller being programmed to:

determine a rotational orientation of the patch, about the central axis and relative to the blood vessel, based at least in part on the first and second temperatures, and generating an alarm, based at least in part on the rotational orientation of the patch, indicating that the rotational orientation of the patch should be changed, wherein:

when the first and third surfaces are disposed on a skin surface of a patient, a difference between a first temperature of the skin surface determined by the first temperature sensor and a second temperature of the skin surface determined by the second temperature sensor is indicative of a position of at least one of the first and second sensors relative to a blood vessel disposed proximate the skin surface.

20. The method of claim 19, wherein:

the controller is configured to determine a core temperature of the patient based on the first and second temperatures, and a correction factor, and the correction factor is determined by the controller based on the difference, the first thermal resistance, and the second thermal resistance.

21. The method of claim 19, further comprising:

disposing the first and second temperature sensors along a first longitudinal axis of the patch extending substantially perpendicular to the central axis, the first and second surfaces extending substantially parallel to the first longitudinal axis; and embedding a third temperature sensor substantially within the second material of the patch such that the third temperature sensor is disposed adjacent to the third surface along the first longitudinal axis.

22. The method of claim 19, further comprising:

disposing the first and second temperature sensors along a first longitudinal axis of the patch extending substantially perpendicular to the central axis, the first and second surfaces extending substantially parallel to the first longitudinal axis; and embedding a third temperature sensor substantially within the second material of the patch such that the third temperature sensor is disposed adjacent to the third surface, the third temperature sensor being disposed along a second longitudinal axis of the patch substantially perpendicular to the first longitudinal axis, the first and third surfaces extending substantially parallel to the second longitudinal axis.

23. The method of claim 19, further comprising:

disposing the first and second temperature sensors along a first longitudinal axis of the patch extending substantially perpendicular to the central axis, the first and second surfaces extending substantially parallel to the first longitudinal axis; and embedding a third temperature sensor substantially within the first material of the patch such that the third temperature sensor is disposed adjacent to the second surface, the third temperature sensor being disposed along the central axis of the patch, the first and second surfaces extending substantially perpendicular to the central axis.

* * * * *